United States Patent
Kopke et al.

(10) Patent No.: US 6,177,434 B1
(45) Date of Patent: Jan. 23, 2001

(54) PREVENTION OR REVERSAL OF SENSORINEURAL HEARING LOSS (SNHL) THROUGH BIOLOGIC MECHANISMS

(75) Inventors: Richard D. Kopke, San Diego, CA (US); Donald Henderson, Clarence, NY (US); Michael E. Hoffer, San Diego, CA (US)

(73) Assignee: The United States of America as represented by the Secretary of the Navy, Washington, DC (US)

(*) Notice: Under 35 U.S.C. 154(b), the term of this patent shall be extended for 0 days.

(21) Appl. No.: 09/126,707

(22) Filed: Jul. 31, 1998

Related U.S. Application Data

(60) Provisional application No. 60/069,761, filed on Dec. 16, 1997.

(51) Int. Cl.[7] .................. A61K 31/52; A61K 31/425; A61K 31/195; A01N 43/90; A01N 43/78
(52) U.S. Cl. .................. 514/266; 514/369; 514/562; 514/547; 514/956
(58) Field of Search .............. 514/21, 179, 180, 514/369, 547, 562, 266

(56) References Cited

U.S. PATENT DOCUMENTS 5,929,041 * 7/1999 Magal et al. .................. 514/44

OTHER PUBLICATIONS

Hu et al., R–phenylisopropyladenosine attenuates noise–induced hearing loss in the chinchilla; Hearing Research; pp. 198–206, Nov. 1997.*

* cited by examiner

Primary Examiner—Shep K. Rose
Assistant Examiner—Donna Jagoe
(74) Attorney, Agent, or Firm—A. David Spevack; Thomas E. McDonnell

(57) ABSTRACT

The invention is accomplished by preventing and/or reversing inner ear damage due to noise or toxins. In part, this is accomplished by upregulating antioxidant enzyme activity by applying agents such as R-N6-Phenylisopropyl adenosine (R-PIA) to the round window membrane of the inner ear or systemically, and/or by also applying agents such as 1-2-oxothiazolidine-4-carboxylic acid (Procysteine) to the round window membrane. Also, the invention is accomplished by giving the compounds systemically. Selective auditory hair cell protection in the face of gentamicin exposure by concomitant delivery of an NMDA antagonist or glial derived neurotrophic factor (GDNF) with the gentamicin. These and additional agents are also accomplished by curtailing activated programmed cell death pathways and/or inducing/enhancing cell repair mechanisms in the inner ear. The agent (s) may be applied before, during or after the noise trauma or toxin exposure.

9 Claims, 10 Drawing Sheets

US 6,177,434 B1

PREVENTION OR REVERSAL OF SENSORINEURAL HEARING LOSS (SNHL) THROUGH BIOLOGIC MECHANISMS

RELATED APPLICATIONS

This Application claims benefit of Provisional Application Ser. No. 60/069,761 filed Dec. 16, 1997.

BACKGROUND OF THE INVENTION

1. Field of the Invention

This invention relates to a method and composition for preventing and/or reversing sensorineural hearing loss (SNHL) or toxin-induced hearing loss. More specifically, this invention relates to the use of agents which augment inner ear antioxidant defenses such as adenosine agonists or up-regulating agents and/or agents which increase inner ear glutathione levels to prevent and/or reverse hearing loss induced by noise or toxin. In addition, this invention covers agents that curtail activated programmed cell death pathways and induce/enhance cell repair mechanisms in the inner ear.

2. Description of the Prior Art

SNHL is a very common problem for service members and civilian government employees. Approximately 450 million dollars is spent annually to compensate service members for hearing loss (1). Despite hearing conservation programs, 20–30% of service members develop compensable hearing loss after 10 years in the service (2). The sense of hearing is critical for combat and operational readiness of soldiers and sailors. Both temporary and permanent hearing threshold impairments decrease the ability to communicate and to detect enemy movements (3). Successful implementation of medical treatment to prevent or reverse SNHL as an augmentation to established hearing conservation programs has the potential to save millions of dollars annually and to significantly improve operational readiness.

It is established by the Center for Disease Control that approximately 30 million people in the U.S. suffer from SNHL (4). The potential for commercialization is very extensive and would include workers in factories, construction operations, communications, and the airline industry to name a few. Many people working in an environment with damaging noise or toxins would potentially benefit from this treatment. In addition, individuals receiving toxic medications for other forms of therapy (i.e. cancer chemotherapy) can suffer SNHL. An idiopathic form of SNHL also exists.

Currently there are no published effective topical medications to prevent or reverse SNHL. There are no published reports of topical, oral, or systemic medications to treat noise-induced hearing loss (NIHL). This invention differs from mechanical noise attenuators or hearing protection devices in that it does not need to be worn and does not decrease hearing acuity as hearing protectors do. Also, this treatment has the potential to reverse SNHL after it is occurred.

Additionally, cisplatin and aminoglycoside antibiotics such as gentamicin represent useful commonly prescribed therapeutic agents which are toxic to the ear and cause sensorineural hearing loss (6,7,15). Gentamicin is used as an agent delivered indirectly to the inner ear via the middle crossing the round window membrane to destroy balance function in an inner ear affected by Meniere's disease (28). One of the limitations of this therapy is that the auditory portion of the inner ear is also often damaged leading to sensorineural hearing loss (29). Thus there is a need to selectively protect the auditory hair cells while eliminating inner ear balance function with the gentamicin.

SUMMARY OF THE INVENTION

Accordingly, an object of this invention is to prevent sensorineural hearing loss and sensorineural hearing loss caused by noise.

A further object of this invention is to reverse sensorineural hearing loss and sensorineural hearing loss induced by noise.

Yet another object of the invention is to prevent and or reverse hearing loss by the topical application of a compound or combination of compounds which increase inner ear glutathione (GSH) levels and/or augment other inner ear antioxidant defenses, and agents that curtail activated programmed cell death pathways and/or induce/enhance cell repair mechanisms in the inner ear.

Another object of the invention is to protect auditory hair cells from toxic injury by cisplatin or gentamicin.

These and additional objects of the invention are accomplished by preventing and/or reversing inner ear damage due to noise or toxins by upregulating antioxidant enzyme activity by applying agents such as R-N6-Phenylisopropyl adenosine (R-PIA) to the round window membrane of the inner ear or systemically, and/or by also applying agents such as 1-2-oxothiazolidine-4-carboxylic acid (Procysteine) to the round window membrane or by giving it systemically. Selective auditory hair cell protection in the face of gentamicin exposure by concomitant delivery of an NMDA antagonist or glial derived neurotrophic factor (GDNF) with the gentamicin. These and additional agents are also accomplished by curtailing activated programmed cell death pathways and/or inducing/enhancing cell repair mechanisms in the inner ear.

The agent (s) may be applied before, during or after the noise trauma or toxin exposure. Currently there is no published effective topical medication to prevent or reverse SNHL, no published effective medication to prevent or reverse NIHL, and no published medical therapy to selectively protect auditory hair cells from gentamicin toxicity. This invention differs from mechanical noise attenuators or hearing protection devices in that it does not need to be worn and does not decrease hearing acuity as hearing protectors do. Also, this treatment has the potential to reverse SNHL or toxic hearing loss after it is occurred.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximations.

DESCRIPTION OF THE PREFERRED EMBODIMENTS

Figure 1:
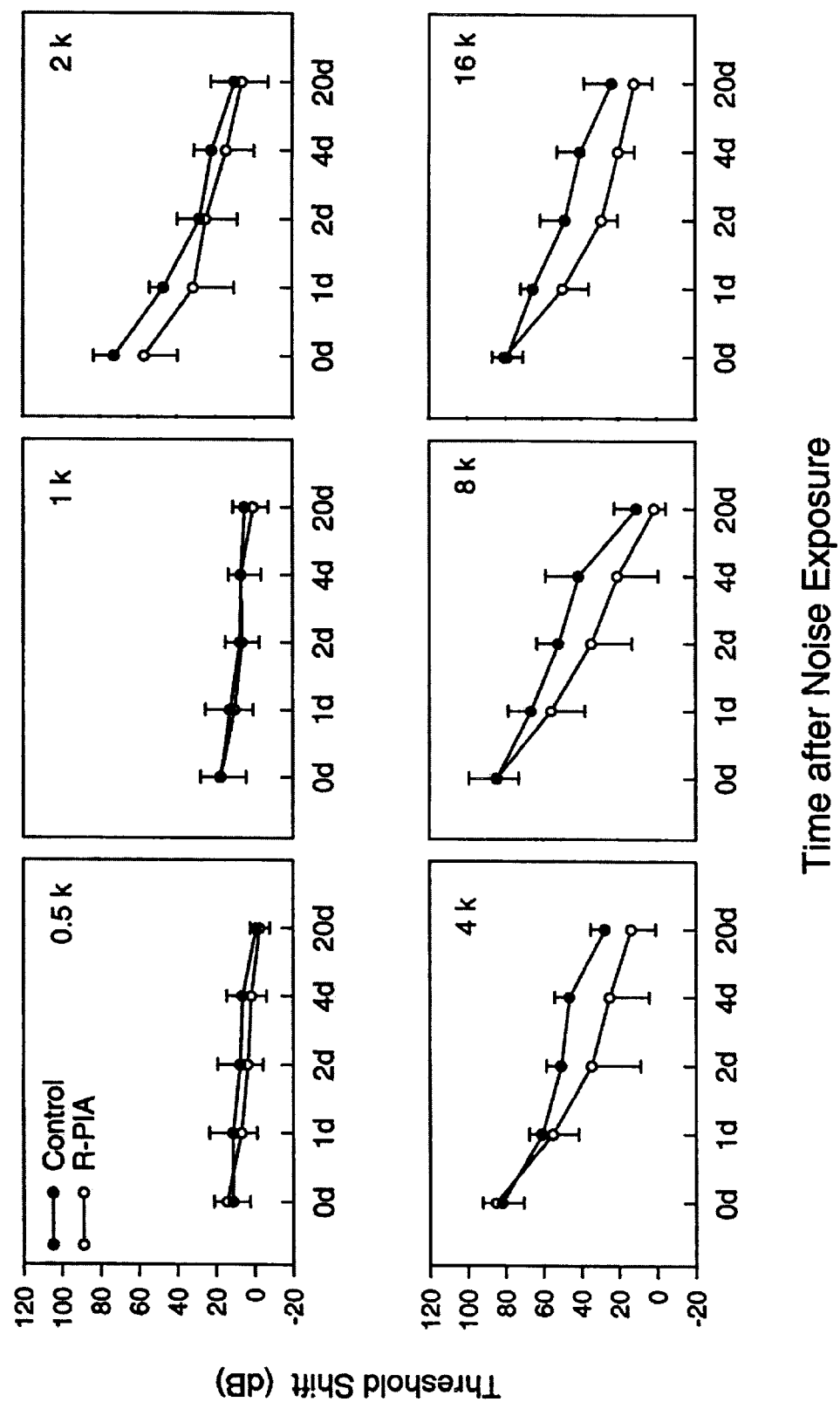
FIG. 1 is a series of graphs which depicts our experimental work with R-PIA in a chinchilla model of SNHL. A $10^{-4}$ M solution of R-PIA was placed on the round window membrane of chinchillas for thirty minutes and saline was placed as a control on round window membrane in the opposite ear. After thirty minutes the fluids were removed, the surgical sites closed and the animals were exposed to 4 kHz octave band noise at 105 dB SPL for thirty minutes. The animals then had hearing thresholds measured at the various frequencies depicted at days 0, 1, 2, 4 and 20 using evoked potentials measured from the inferior colliculus. R-PIA treated ears showed a faster and more complete recovery of hearing thresholds than ears treated with saline. In fact there was significantly less permanent hearing threshold shift in R-PIA treated ears compared to saline treated ears at 4, 8 and 16 kHz.

The invention is accomplished by preventing and/or reversing inner ear damage due to noise or toxins by upregulating antioxidant enzyme activity by applying agents such as R-N6-Phenylisopropyl adenosine (R-PIA) to the round window membrane of the inner ear or systemically, and/or by also applying agents such as 1-2-oxothiazolidine-4-carboxylic acid (Procysteine) to the round window membrane or by giving it systemically. Selective auditory hair cell protection in the face of gentamicin exposure by concomitant delivery of an NMDA antagonist or a trophic factor such as GDNF with the gentamicin. These and additional agents are also accomplished by curtailing activated programmed cell death pathways and/or inducing/enhancing cell repair mechanisms in the inner ear.

These agents can be administered orally, intravenously, topically onto the surface of the round window membrane of the ear, or topically elsewhere in the middle or inner ear. The preferable systemic administration method is orally and the preferable topical administration is via a catheter onto the surface of the round window membrane of the ear.

Reactive oxygen intermediates (ROI) have now been associated with deafness due to aminoglycoside antibiotics (i.e. gentamicin), chemotherapeutic agents (i.e. cisplatin), noise-induced hearing loss and closed head injury and (6, 7, 5, 8). Cisplatin and noise exposure are both associated with decreases in cochlear and hair cell reduced glutathione (GSH) a major intracellular free radical scavenger and reducing compound (9,5). Depletion of cellular GSH results in increased calcium release from intracellular stores as well as inhibition of calcium extrusion, producing a marked increase in cytosolic calcium concentration. The rise in cytosolic calcium then triggers cytotoxicity which may take the form of apoptosis (10). Oxidative stress resulting in reduced cellular GSH can lead to apoptosis in neural as well as non-neural cells (11).

Possible mechanisms by which noise may induce ROI in the cochlea may include as a secondary event to ischemia-reperfusion due to temporary vasoconstriction (12), directly from the effects of sound energy on oxygenated perilymph (13), as a result of noise-induced calcium influx through trauma-induced cell membrane microbreaks (14) or as a by-product of glutamate excitoxicity including nitric oxide (NO) and peroxynitrite ROI damage (15).

Considerable evidence is accumulating that implicates ROI in the cochlear damage associated with some acoustic trauma. Exposure of chinchillas to "conditioning" noise leads to the upregulation of the activity of several antioxidant enzymes (16). High level noise exposure is associated with accumulation of superoxide anion in the stria vascularis (17) and other ROI (18) in the cochlea. Also, noise exposure is associated with an increase in perilymph GSH levels (22), while outer hair cell GSH levels decline. As in the case of cisplatin toxicity, inhibition of GSH synthesis using buthionine sulfoximine (BSO) enhances the hair cell damage and hearing loss associated with noise exposure (18). Quirk et al. published that an antioxidant lipid peroxidase inhibitor prevented temporary threshold shifts in noise-exposed rats (19). Super oxide dismutase-polyethylene glycol and allopurinol, two free radical scavengers, were found to attenuate cochlear action potential and cochlear microphonic threshold shifts when given before and during damaging noise exposure (22). An adenosine agonist which can upregulate antioxidant enzyme activity in the cochlea can prevent outer hair cell death and permanent hearing loss in chinchilla (5) and a GSH prodrug administered prior to noise exposure was found to reduce hearing loss in guinea pigs (18). Two NMDA receptor antagonists were found to prevent auditory hair cell damage and hearing loss in animals exposed to gentamicin and other aminoglycosdes (27). The proposed mechanism is that gentamicin damages the auditory hair cells by combining with NMDA receptors for the auditory neurotransmitter glutamate causing glutamate excitotoxicity. By blocking access of the gentamicin to the NMDA receptor the NMDA antagonists prevent the glutamate excitotoxicity, hair cell loss and hearing reduction (27). Since the vestibular hair cells and neurons utilize a different neurotransmitter and receptor system the auditory hair cells can selectively be protected while gentamicin ablates the vestibular system by including an NMDA antagonist with the gentamicin or preceding the gentamicin.

Upregulating and augmenting the inner ear's defenses against ROI thus has the potential to reduce hearing loss due to all these etiologies. We have shown that enhancing inner ear antioxidant defenses can reduce inner ear cochlear hair cell loss and/or hearing loss due to noise and cisplatin and others have shown that different antioxidant strategies may reduce aminoglycoside ototoxicity.

The invention involves augmenting the inner ear's antioxidant defenses either prior to (protection) or after (rescue) the toxic or traumatic insult by increasing inner ear antioxidant enzyme activity, by increasing the inner ear antioxidant levels, by reducing glutamate excitotoxicity or by combining these treatment modalities. More specifically, the therapeutic strategy involves increasing antioxidant enzyme levels in the inner ear through the application of agents such as the adenosine agonist R-PIA or other similar agents, or through the application of antiapoptotic agents or trophic factors (growth factors) which may also upregulate antioxidant enzyme levels. Increasing inner ear antioxidant levels would primarily be aimed at increasing inner ear glutathione (GSH) levels. By itself, GSH is relatively ineffective at increasing intracellular GSH levels as it is not well transported into most cells (23). Therefor the invention calls for utilizing compounds which can be transported into the inner ear hair cells and then synthesized into GSH. These compounds would include L-2-oxothiazolidine-4-carboxylic acid (OTC), L-N-acetylcysteine (L-NAC), methionine and S-adenosyl-L-methionine (SAMe) as well as other agents which could increase inner ear glutathione levels. GSH formation is under feed back inhibition in that adequate GSH levels inhibit the rate limiting enzyme for GSH synthesis, γ-glutamyl cysteine synthase (23). For this reason, the combination of an agent which upregulates the antioxidant enzyme activity (R-PIA upregulates γ-glutamyl cysteine synthase activity in the inner ear) with a substrate for GSH (i.e. OTC) is more likely to have a protective or rescue effect on the inner ear when ROI are involved in creating damage. This invention would include the use of a combination of agents such as the addition of uric acid as a free radical scavenger or single agents depending on safety and efficacy. These agents might be delivered systemically, in the middle ear or directly in the inner ear. NMDA antagonists would include agents such as dizocilpine or ifenprodil or similar agents (27).

Upregulating adenosine effects in the inner ear may have additional beneficial effects other than upregulating antioxidant enzyme activity. Adenosine upregulation in neural tissue has been demonstrated to decrease release of potentially damaging excitotoxic amino acids (24) such as glutamate (the primary cochlear neurotransmitter) and thereby limit NO production and damage (25). Also seen is a beneficial vasodilator effect, calcium homeostasis maintenance effect and a cell membrane stabilizing effect (24). Given systemically, adenosine agonists may have unwanted side effects including hypotension, cardiac depression and hypothermia and these agents may not cross from the blood to the inner ear through the blood labyrinthine barrier (26). These problems may be dealt with by applying the drug to the round window membrane, by utilizing drugs such as acadesine and AICA Riboside which act as an adenosine agonist only in ischemic tissues (30,31) or by utilizing adenosine agonists that have specific uptake in the inner ear. Adenosine effects can also be increased by blocking adenosine breakdown using adenosine deaminase inhibitors (24).

Many of the GSH substrates and adenosine agonists have a short effective or systemic half-life. Therefor this invention may include the use of embodiments that increase the effective half-life of the drug when given systemically and may include an infusion device or pump or sustained release polymer for sustained systemic release.

Having described the invention, the following examples are given to illustrate specific applications of the invention including the best mode now known to perform the invention. These specific examples are not intended to limit the scope of the invention described in this application.

This invention functions to prevent or reverse toxic or noise induced hearing loss (SNHL) through biologic mechanisms. Reactive oxygen intermediates (ROI) are responsible for inner ear damage due to loud noise and toxins. Inner ear damage due to ROI can be reduced by augmenting the inner ear's antioxidant defenses. The invention involves preventing and/or reversing inner ear damage due to toxins or noise by upregulating antioxidant enzyme activity by applying adenosine agonists such as R-N6-Phenylisopropyl adenosine (R-PIA), acadesine or adenosine deaminase inhibitors to the round window membrane of the inner ear, and/or by also applying 1-2-oxothiazolidine-4-carboxylic acid (Procysteine) or other glutathione prodrugs to the round window membrane or by giving them systemically with or without free radical scavengers such as uric acid (32). The agent(s) may be applied before, during or after the noise trauma or toxic exposure. Selective protection of auditory hair cells in patients receiving intratympanic gentamicin therapy by preceding the gentamicin therapy with an NMDA antagonist and giving it concomitantly with the gentamicin in the same vehicle. Currently there is no published effective medication to prevent or reverse SNHL. This invention differs from mechanical noise attenuators or hearing protection devices in that it does not need to be worn and does not decrease hearing acuity as hearing protectors do. Also, this treatment has the potential to reverse SNHL after it is occurred.

Many specific clinical examples for the use of these therapies can be described. Workers in a high-risk noise environment could be given oral agents to enhance antioxidant ear defenses prophylactically. Persons exposed to unexpected loud noise with subsequent hearing loss could be given systemic or intraear therapies to rescue and reverse the hearing loss. Patients receiving cisplatin or aminoglycoside antibiotics or other drugs with potential ear toxicities could be given the protective agents before, during or after the toxin to prevent or reverse hearing loss. Patients with Meniere's disease undergoing intratympanic gentamicin therapy could be given NMDA antagonists with or without other protective agents at the same time or preceding the gentamicin therapy, possibly in the same delivery vehicle.

Having described the invention the following examples are given to illustrate specific applications of the invention including the best mode now known to perform the invention.

EXAMPLE 1

Figure 2:
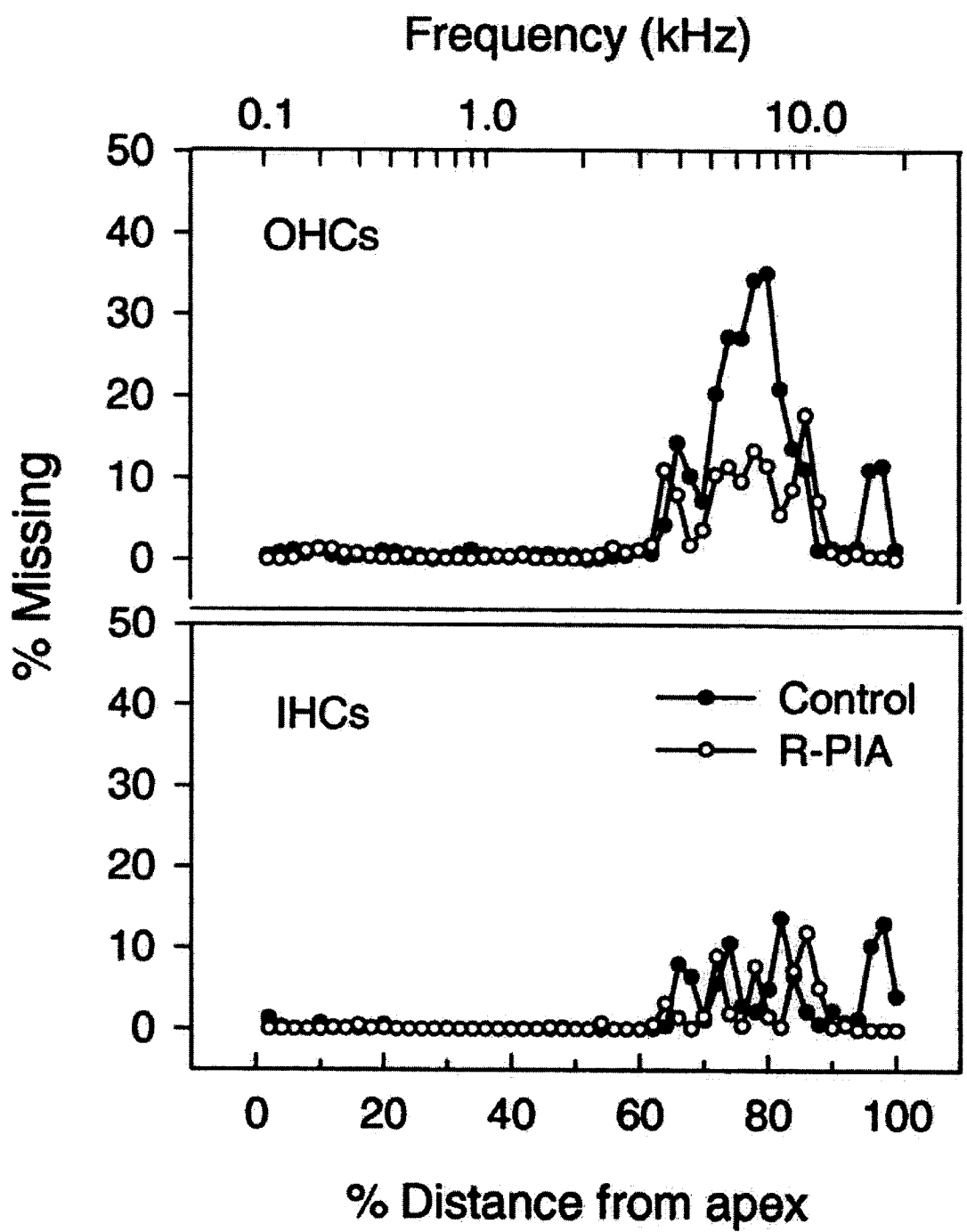
FIG. 2 is two graphs which depicts the data from these same animals showing inner and outer hair cell losses. Inner hair cell losses were minimal in both conditions but there was a fourfold reduction in outer hair cell loss in the R-PIA treated ears compared to saline control ears consistent with the reduction in hearing loss seen in ears treated with R-PIA. The details of this study have been submitted and recently accepted for publication in a peer-reviewed journal (5).

In FIG. 1 noise induced permanent threshold shifts were prevented in the Chinchilla model by the application of a dilute ($10^{-4}$ molar) solution of R-PIA directly onto the round window membrane for thirty minutes. What is demonstrated in this figure is a significant reduction in permanent hearing loss in the R-PIA treated ears compared to control ears. FIG. 2 shows that the R-PIA treated ears had a four-fold reduction in outer hair cell loss compared to control ears. These data of hair cell counts are from the same animals which underwent hearing testing.

EXAMPLE 2

Figure 3:
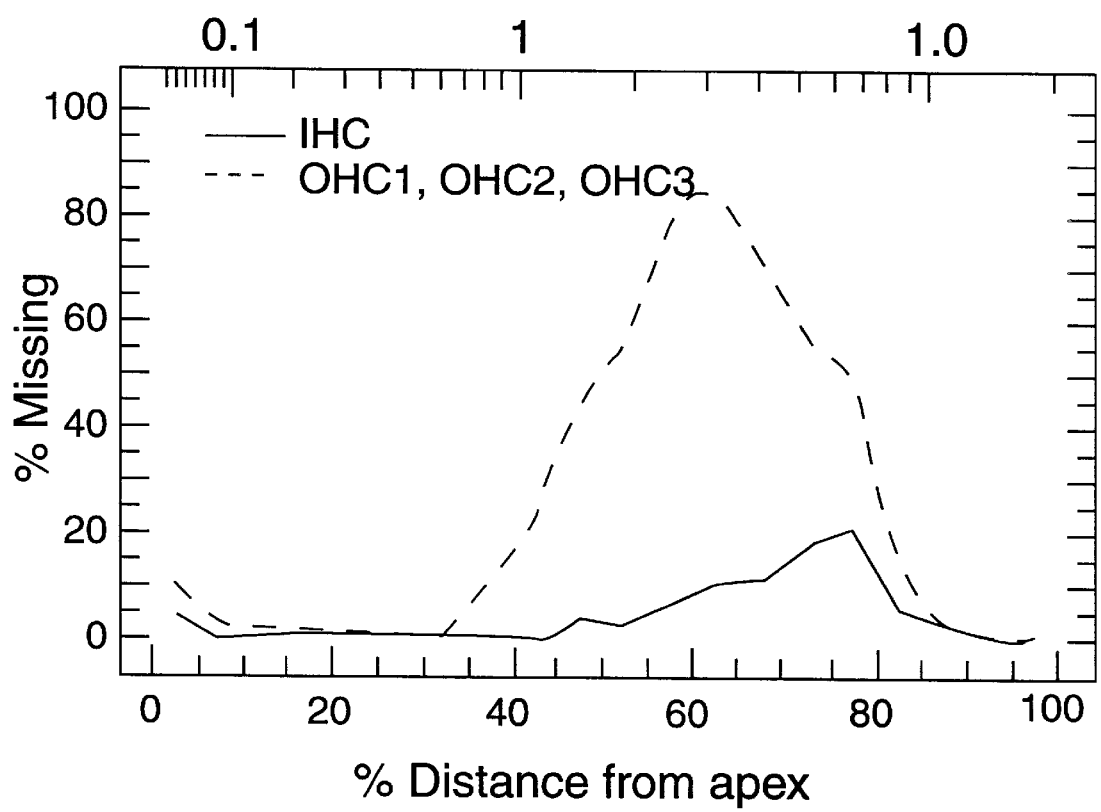
FIG. 3 is a graph depicting the percentage of missing hair cells from animals receiving round window membrane RPIA treatment in the right ear, as above, after impulse noise exposure mimicking a 50-salvo volley of M-16 fire.
Figure 4:
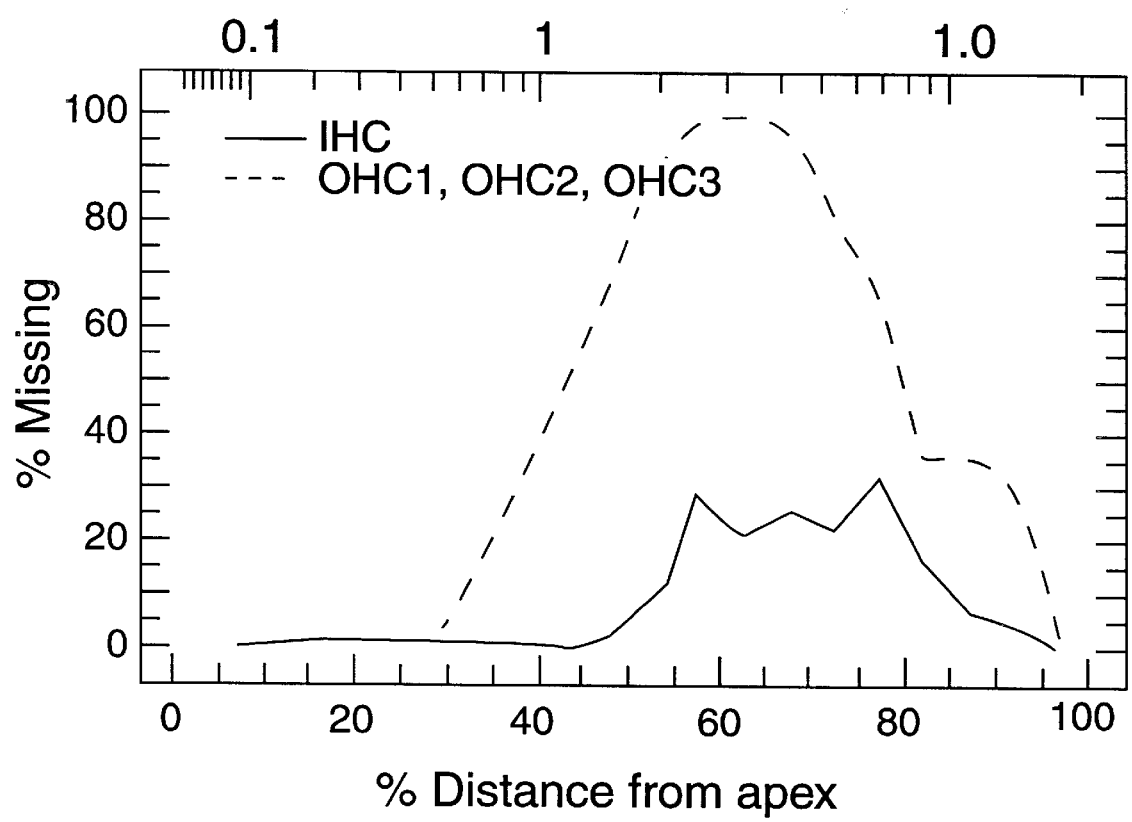
FIG. 4 is a graph depicting the percentage of missing hair cells from the left (untreated ear) of the same animals, as above, after impulse noise exposure mimicking a 50-salvo volley of M-16 fire.

FIGS. 3 & 4 illustrate data from Chinchilla exposed to simulated M-16 rifle fire impulse noise (50-salvo volleys). These animals received R-PIA treatment as outlined above (by the application of a dilute ($10^{-4}$ molar) solution of R-PIA directly onto the round window membrane for thirty minutes) with saline as a control on the round window membrane of the opposite ear. FIGS. 3 and 4 depict the percentage of missing inner and outer hair cells quantified in the inner ears of animals euthanized after the noise exposure. These figures demonstrate a significant reduction of inner and outer hair cell loss in the R-PIA treated ears compared to control ears.

Experimental results show a reduction of permanent hearing loss in R-PIA treated ears as compared to saline treated (control) ears at a variety of different frequencies.

Other tests show a reduction of permanent hearing loss in R-PIA treated ears as compared to ears that received no treatment. The results of both these tests show the frequency specific evoked potential threshold shifts from the same Chinchilla prior to and after noise exposure (out to 20 days post-exposure). These results demonstrate a signficant reduction in permanent hearing loss at a number of different frequencies.

EXAMPLE 3

Figure 7:
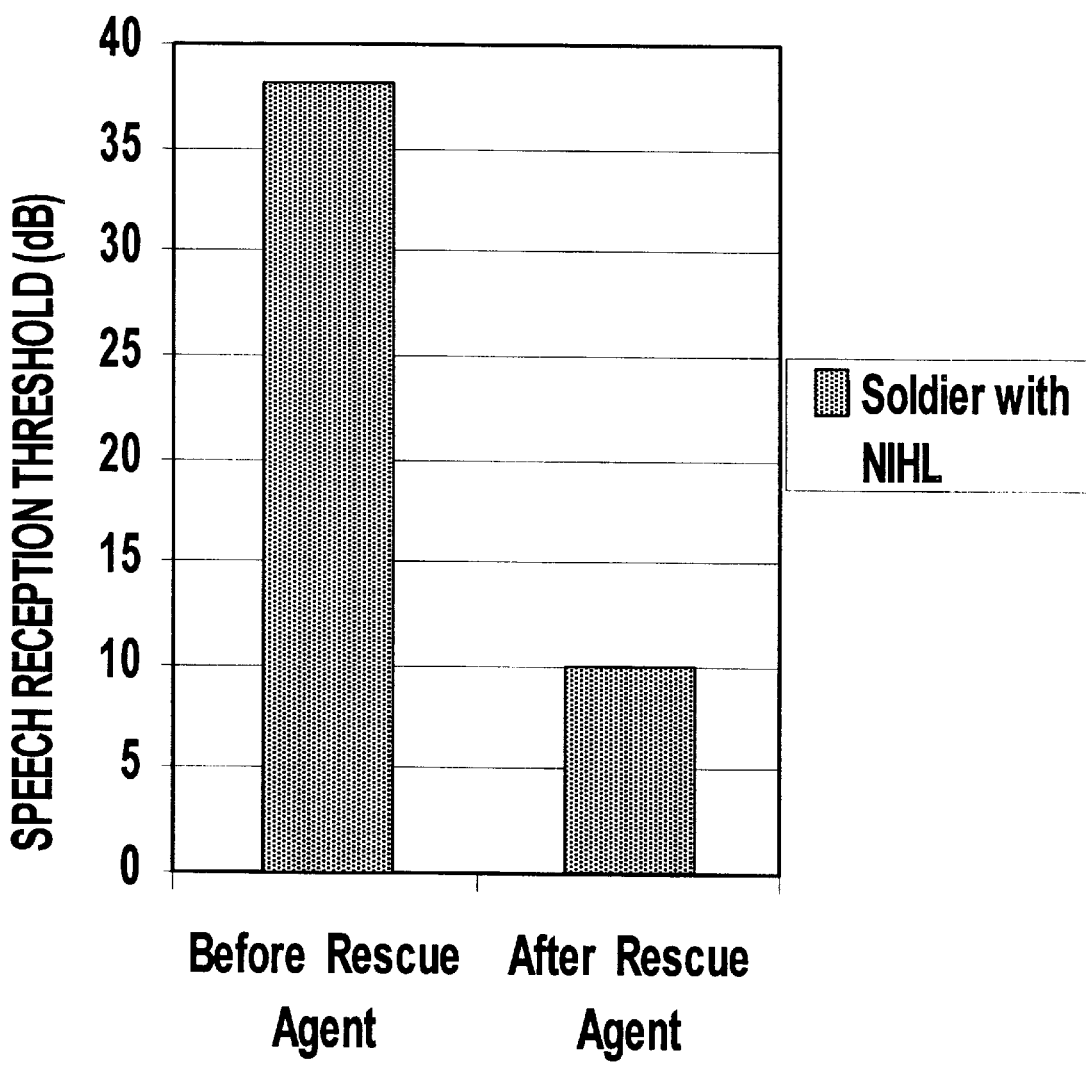
FIG. 7 is a bar graph comparing the speech reception threshold values of an individual who suffered noise induced hearing loss before and after administration of an oral rescue agent.
Figure 8:
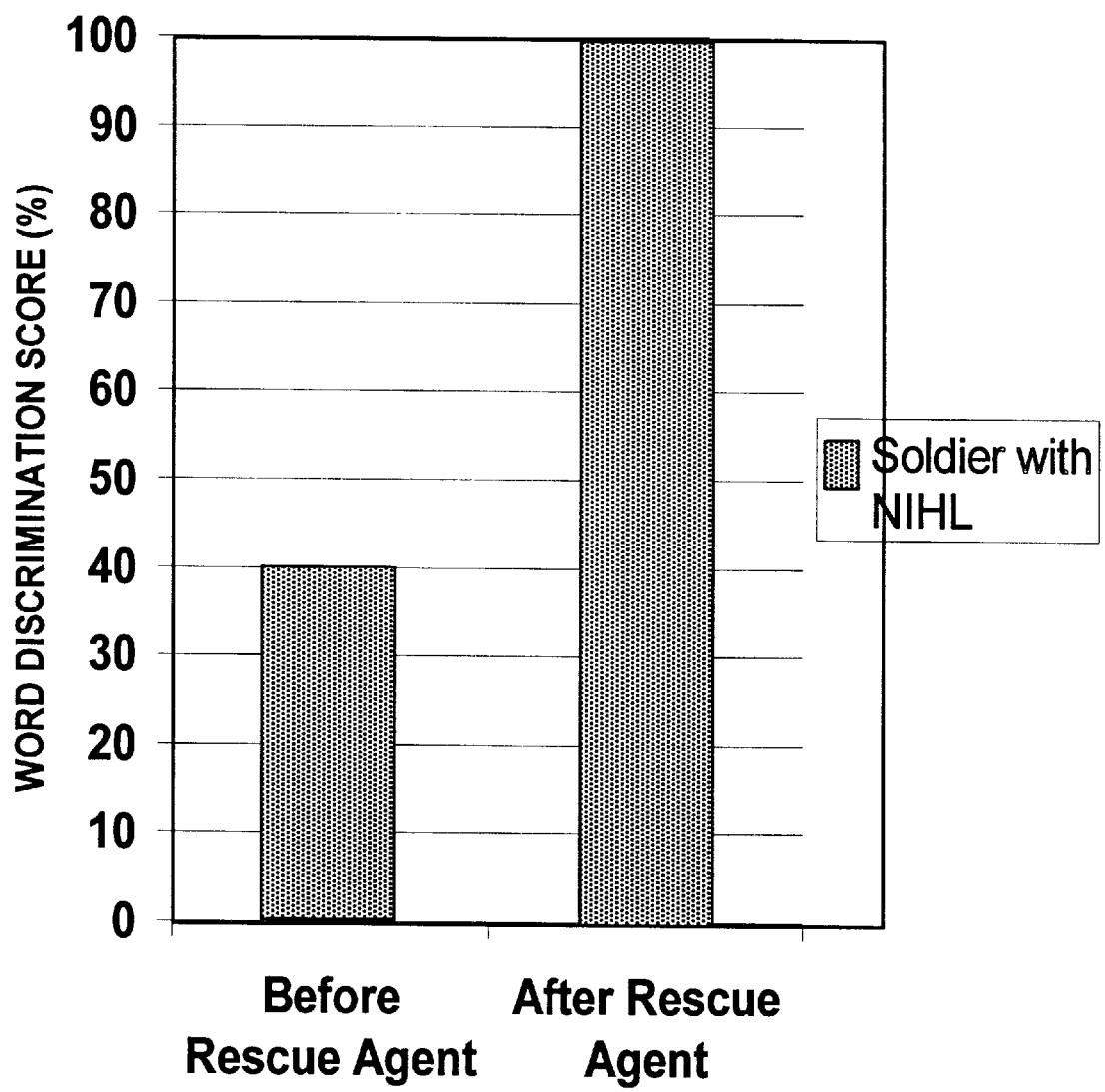
FIG. 8 is a bar graph comparing the word discrimination scores of an individual who suffered noise induced hearing loss before and after administration of an oral rescue agent.

An Army Infantryman lost his hearing protection in one ear during a live fire training evolution. He suffered a moderate to severe hearing lost in the effected ear. He received treatment in the form of an initial dose of 70 mg/kg of L-N-acetyl cysteine (LNAC) by mouth followed by 35 mg/kg LNAC by mouth QID for seven days. FIG. 7 depicts the complete recovery of a moderately elevated speech reception threshold. FIG. 8 depicts the complete recovery of a severely impaired word discrimination ability. Our conclusion is that this soldier's hearing recovered after administration of this agent. This degree of hearing recovery is greater than usually seen with this degree of hearing impairment due to noise.

EXAMPLE 4

Figure 9:
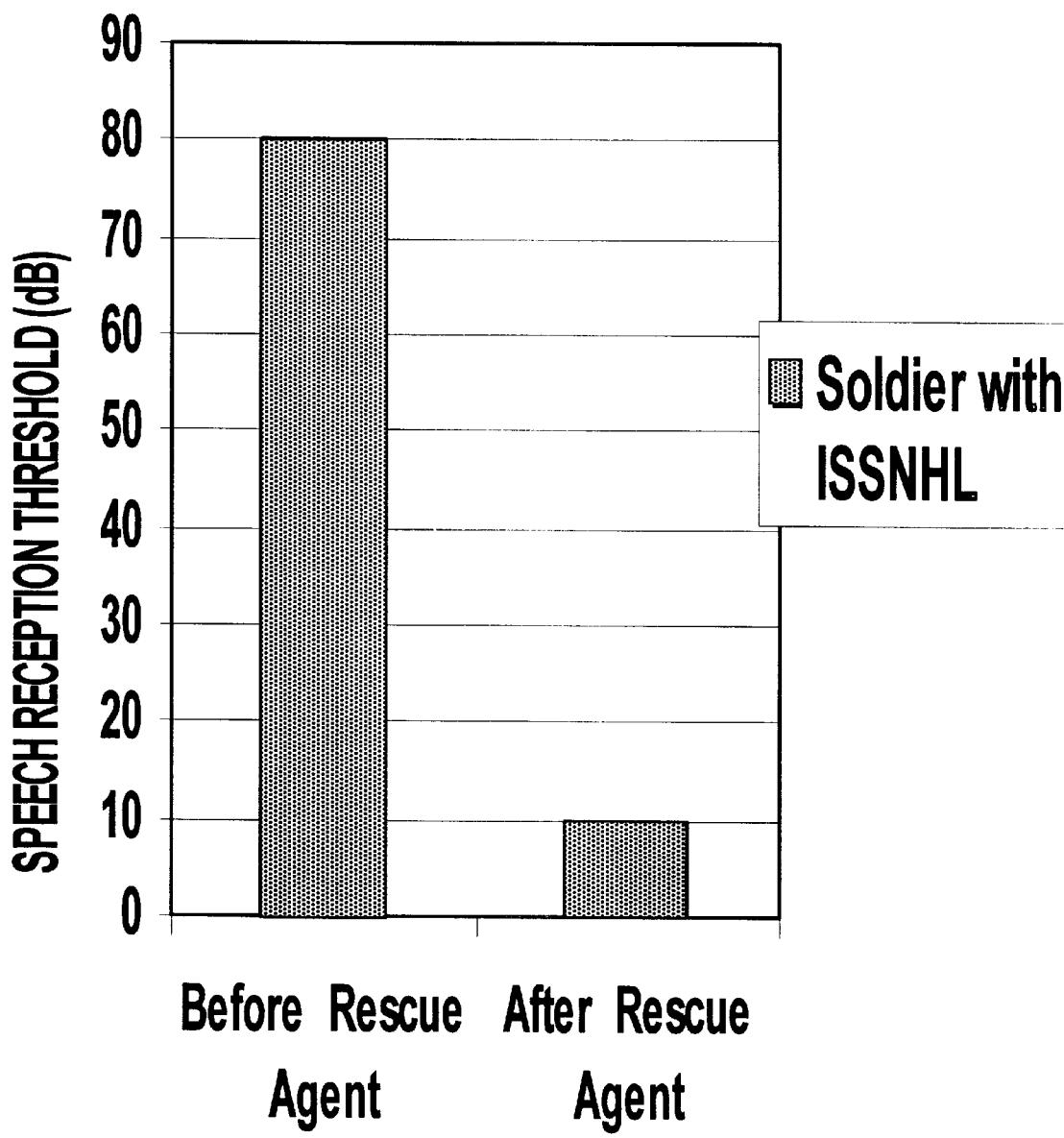
FIG. 9 is a bar graph comparing the speech reception threshold values of an individual who suffered an idiopathic sensorineural hearing loss before and after administration of a topical rescue agent.
Figure 10:
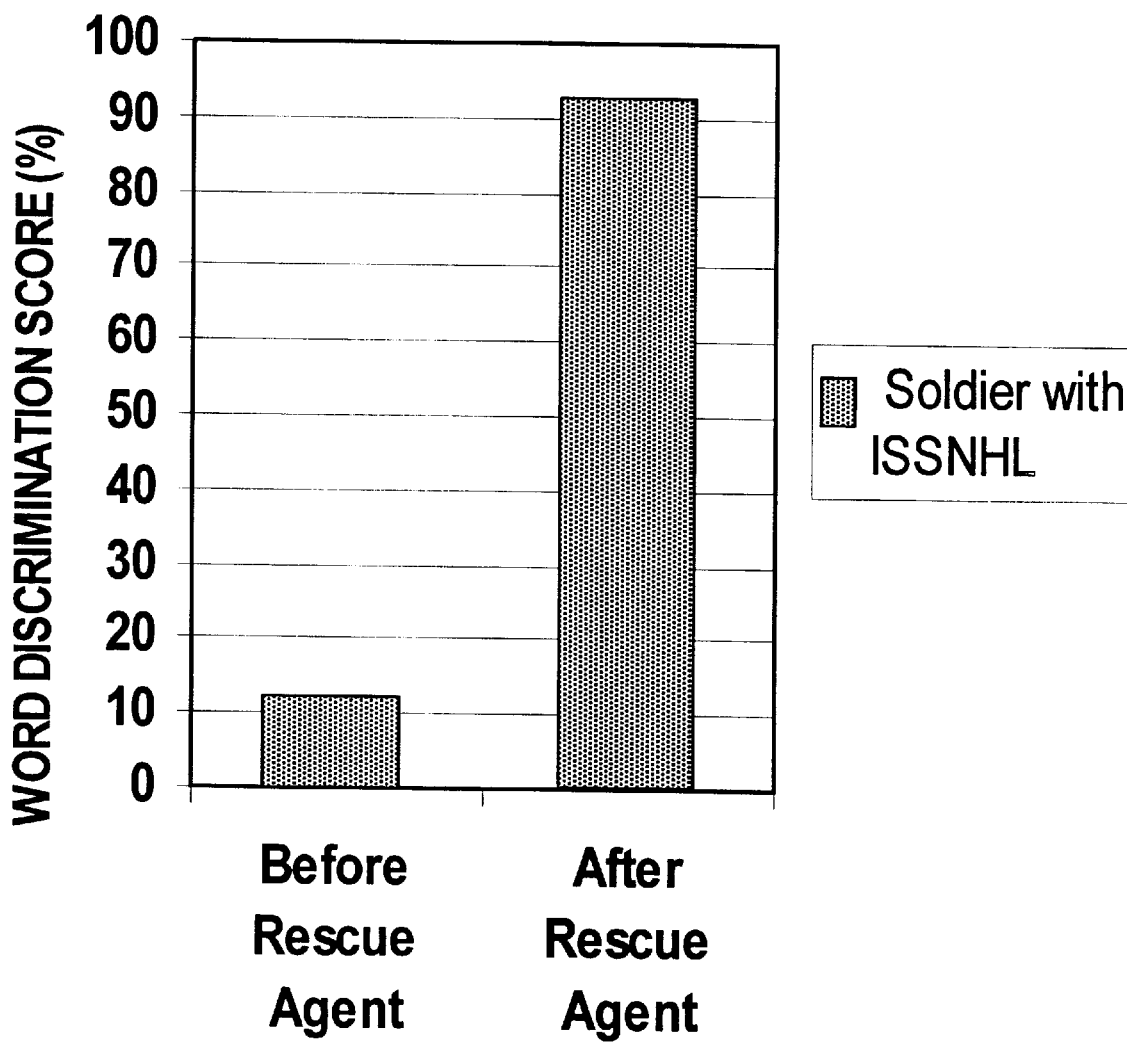
FIG. 10 is a bar graph comparing the word discrimination scores of an individual who suffered an idiopathic sensorineural hearing loss before and after administration of a topical rescue agent.

A 43 year old Army Sergeant noted the sudden onset of a severe hearing loss and tinnitus in her left ear. She was initially given one week of conventional therapy with oral prednisone and a trial of close observation. She had no response to this treatment regimen and two weeks after experiencing the hearing loss she was treated with topical methylprednisolone. The topical methylprednisolone was administered in a round window micro-catheter (IntraEar Corporation, Denver, Colo.) via a method developed by our group. The methylprednisolone was given in a concentration of 125 mg/ml. The catheter was pre-loaded with 0.125 ml of this compound after the catheter was secure in the round window niche. The catheter was then attached to a battery operated pump (Disetronics, Inc) which pumped the methylprednisolone into the catheter at 10 ul/hour for 14 days. FIG. 9 depicts the complete recovery of the severely elevated speech reception threshold back to normal levels. FIG. 10 depicts the complete recovery of the profoundly impaired word discrimination ability after administration of the medicine. The patient's tinnitus was completely resolved after treatment. Since this individual had failed conventional therapy, the outlook for recovery without the new treatment was less than 15%.

EXAMPLE 5

Figure 11:
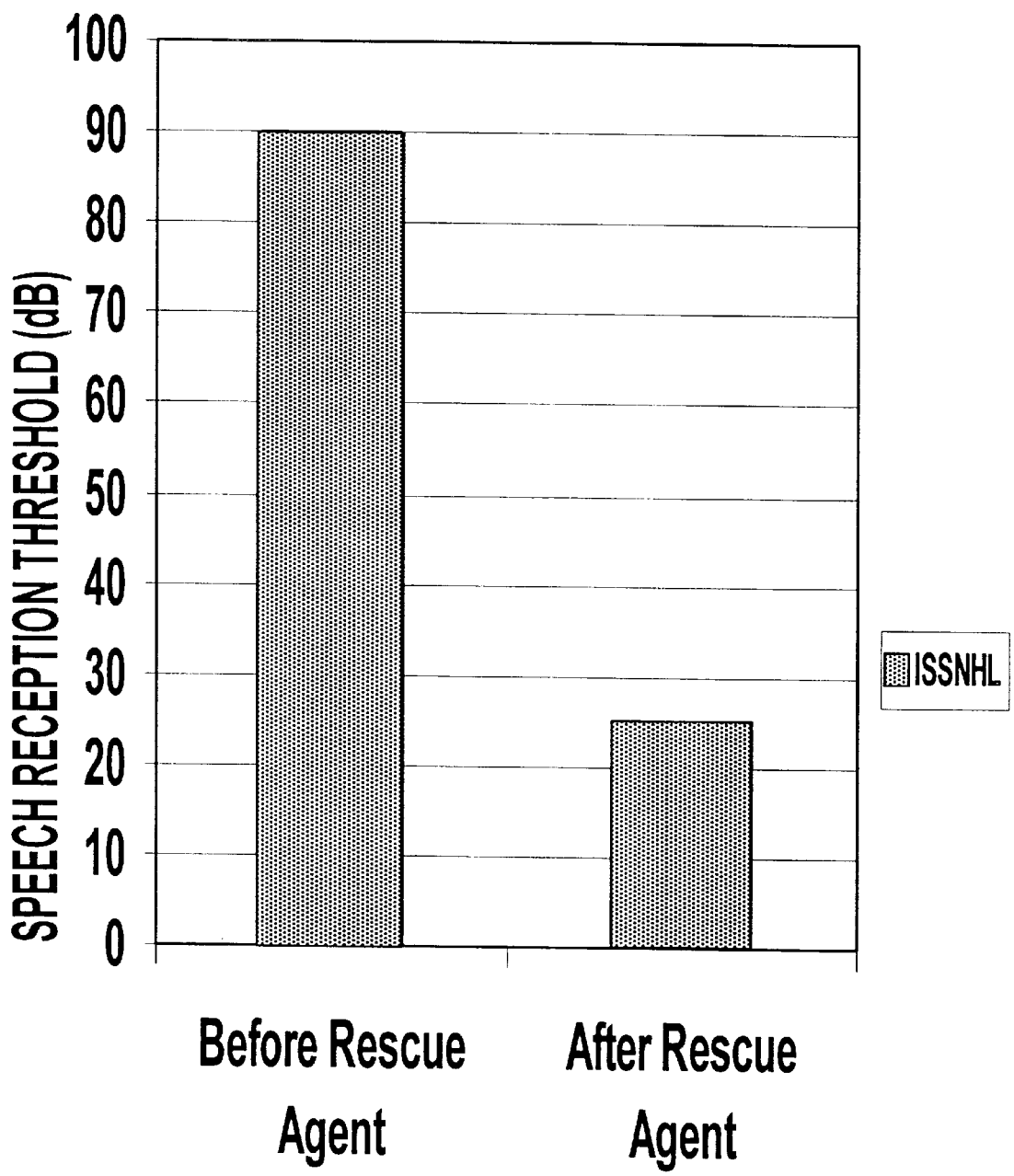
FIG. 11 is a bar graph comparing the speech reception threshold values of another individual who suffered an idiopathic sensorineural hearing loss before and after administration of a topical rescue agent.
Figure 12:
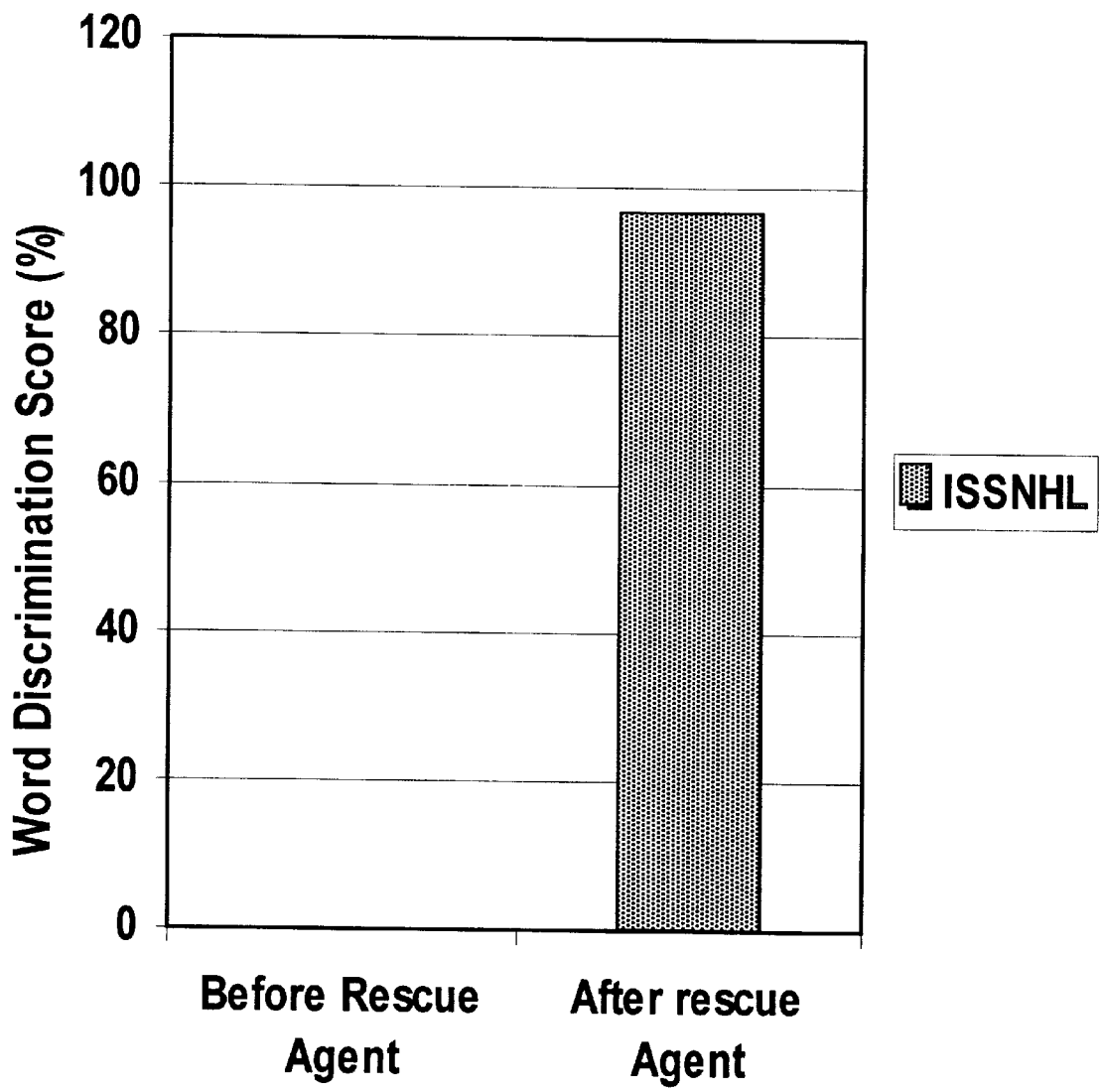
FIG. 12 is a bar graph comparing the word discrimination scores of another individual who suffered an idiopathic sensorineural hearing loss before and after administration of a topical rescue agent.

A 48 year old Ophthalmologist noted the sudden onset of a severe hearing loss and tinnitus in his right ear. He was initially given three weeks of conventional therapy with oral prednisone for 10 days and a trial of close observation. He had no response to this treatment regimen and three weeks after experiencing the hearing loss he was treated with topical methylprednisolone. The topical methylprednisolone was administered in a round window micro-catheter (IntraEar Corporation, Denver, Colo.) via a method developed by our group. The methylprednisolone was given in a concentration of 125 mg/ml. The catheter was pre-loaded with 0.125 ml of this compound after the catheter was secure in the round window niche. The catheter was then attached to a battery operated pump (Disetronics, Inc) which pumped the methylprednisolone into the catheter at 10 ul/hour for 14 days. FIG. 11 depicts the complete recovery of the profoundly elevated speech reception threshold back to normal levels. FIG. 12 depicts the complete recovery of the profoundly impaired word discrimination ability after administration of the medicine. The patient's tinnitus was completely resolved after treatment. Since this individual had failed conventional therapy, the outlook for recovery without the new treatment was less than 15%.

REFERENCES

1. Ohlin, D. U.S. Army Center for Health Promotion and Preventative Medicine, (personal communication)
2. Ohlin, D. Hearing Conservation Special Study No.51-01-PM82-93, 15 Years Revisited: The Prevalence of Hearing Loss Among Selected U.S. Army Branches, 1992
3. Price G., Kalb J., Garinther G., Toward A Measure of Auditory Handicap In The Army. Ann. Otol. Rhinol. Laryngol. 1989; 98: 42–52
4. Center for Disease Control. Leading work related diseases and injuries-United States MMWR. 1983; 32:24–6, 32
5. Hu B., Zheng X., McFadden S., Kopke R., Henderson D., R-PIA attenuates noise-induced hearing loss in the chinchilla. Hear. Res. 1997; in press
6. Clerici W., Hensley K., DiMartino D., Butterfield D., Direct detection of ototoxicant-induced reactive oxygen species generation in cochlear explants. Hear. Res. 1996; 98:116–124
7. Kopke R., Liu., Gabaizadeh R., Jacono A., Feghali J., Spray D., Garcia P., Steinman H., Malgrange B., Ruben R., Rybak L., Van De Water T., The use of organotypic cultures of Corti's organ to study the protective effects of antioxidant molecules on cisplatin induced damage of auditory hair cells. Am. J.Otol. 1997; in press
8. Clerici W., Zhang L., Yang, L., Parasad M., Spin trap protection against fluid percussion traumatic brain injury-induced auditory dysfunction Abstracts of the 20th ARO Midwinter Meeting. St. Petersburg, Fla. 1997 (Abstract 451)
9. Ravi R., Somani S., Rybak L., Mechanism of cisplatin ototoxicity: antioxidant system. Pharmacol. Toxicol. 1995; 76:386–394
10. Bellomo G., Orrbenius S., Altered thiol and calcium homeostasis in oxidative hepatocellular injury. Hepatology 1985; 5:876–82
11. Ratan R., Murphy T., Baraban. Macromolecular synthesis inhibitors prevent oxidative stress-induced apoptosis in embryonic cortical neurons by shunting cysteine from protein synthesis to glutathione. J. Neurosci. 1994; 14(7):4385–4392
12. Quirk W., Seidman M., Cochlear vascular changes in response to loud noise. Am. J. Otol. 1995; 16:322–325
13. Landi L., Pasquali P., Cabrini L., Effect of oxygen free radicals on ubiquinone in aquieous solution and phospholipid vesicles. Biochim. Biophys. Acta. 1987; 902:200–206
14. Mulroy M., Henry W., Exposure to loud noise induces temporary microlesions in the plasma membranes of 15. Ernfors P., Canlon B., Aminoglycoside excitement silences hearing. Nature Med. 1996; 2(12):1313–14
16. Jacono A., Kopke R., Vugmeyster L., et al Changes in cochlear antioxidant enzyme levels after conditioning noise exposure in the chinchilla. Abstracts of the 19th ARO Midwinter Meeting. St. Petersburg, Fla. 1996 (Abstract 132).
17. Yamane H., Nakai Y., Takayama M., Konishi K., Iguchi H., Nakagawa T., Shibata S., Kato A., Sunami K., Kawakatsu C., The emergence of free radicals after acoustic trauma and strial blood flow. Acta Otolaryngol. Suppl (Stockholm). 1995; 519:87–92
18. Liu A., Experimental study on the mechanism of free radical in blast trauma induced hearing loss. Chinese J. Otorhinolaryngol. 1992; 27:24–26
19. Bobbin R., Fallon M., LeBlanc C., Baber A., Evidence that glutathione is the unidentified amine (Unk 2.5) released by high potassium into cochlear fluids. Hear. Res. 1995; 87:49–54
20. Yamasoba T., Nuttall A., Miller J., The role of glutathione in protection against noise-induced hearing loss. Poster 32, 1997 Annual Meeting AAOHNS, San Francisco Calif.
21. Quirk W., Shivapuja B., Schwimmer C., Seidman., Lipid peroxidation inhibitor attenuates noise-induced temporary threshold shifts. Hear. Res. 1994; 74:217–20
22. Seidman M., Shivapuja B., Quirk W., The protective effects of allopurinol and superoxide dismutase on noise-induced cochlear damage. Otollaryngol Head Neck Surg 1993; 109: 1052–56
23. Meister A., Glutathione deficiency produced by inhibition of its synthesis, and its reversal: applications in research and therapy. Pharmacol Ther. 1991; 51:155–94
24. Miller L., Hsu C., Therapeutic potential for adenosine receptor activation in ischemic brain injury. J.of Neurotrama. 1992; 9:S563–S577
25. Fessenden J., Coling D., Schacht J., Detection and characterization of nitric oxide synthase in the mammalian cochlea. Brain Res. 1994; 668:9–15
26. Rudolphi K., Schubert P., Parkinson F., Fredholm B., Neuroprotective role of adenosine in cerebral ischaemia. Trends Pharamacol Sci. 1992; 13:439–445
27. Basile A., Huang J., Xie C., Webster D., Berlin C., Skolnick P. N-methyl-D-aspartate antagonists limit aminoglycoside antibiotic-induced hearing loss. Nature Medicine 1996; 2(12); 1338–1343
28. Balough B J, Hoffer M E, Wester D, and O'Leary M J:_ Destructive ototoxic medicines: The kinetics of gentamicin uptake in the inner ear of Chinchilla Laniger following middle ear administration in a sustained release vehicle, In Press Otoalryngol Head Neck Surgery
29. Hoffer M E, Balough B, Wester D, Kopke R D, and O'Leary M J:_Destructive ototoxic medicines: "Finding the therapeutic window into the inner ear" in Endolymphatic Sac Surgery, Arenberg I and Graham M (eds). Singular Publishing, 1998 (in press)
30. Gruber H E, Hoffer M E, McAllister D R, Laikind P K, Lane T, Schmid-Schoenbein G, Engler R L: Increased Adenosine Concentration in Blood from Ischemic Myocardium by AICA Riboside: Effects on Flow, Granulocytes, and Injury. Circulation, 80(5): 1400–1411, 1989.
31. Mullane K. Acadesine: the prototype adenosine regulating agent for reducing myocardial ischaemic injury. Cardiovascular Research. 1993; 27: 43–47
32. Hooper D., Bagasra O., Marini J., Zborek A. et al. Prevention of experimental allergic encephalomyelitis by targeting nitric oxide and peroxynitrite: implications for the treatment of multiple sclerosis. Proc. Natl Acad Sci USA, 94(6):2528–2533, 1997.

Obviously, many modifications and variations of the present invention are possible in light of the above teachings. It is therefore to be understood that, within the scope of the appended claims, the invention may be practiced otherwise than as specifically described.

What is claimed is:

1. A method of reducing, restoring, or protecting a subject against hearing loss by administering to a subject a pharmaceutically effective amount of antioxidant compounds.

2. The method of claim 1 wherein the compound is selected from the group consisting of R-PIA, L-NAC, and glutathione monoethyl ester.

3. The method of claim 1 wherein the compound upregulates antioxidant enzyme activity.

4. The method of claim 3 wherein the compound that upregulates antioxidant enzyme activity is R-PIA.

5. The method of claim 1 wherein the compound is administered systemically.

6. The method of claim 5 wherein the compound is administered orally.

7. The method of claim 1 wherein the compound is administered topically.

8. The method of claim 7 wherein the compound is administered topically through a catheter to the round window membrane of the inner ear.

9. The method of claim 1 of protecting against hearing loss by the oral administration of antioxidant compounds.

* * * * *